US00PP24294P3

(12) United States Plant Patent
Detweiler

(10) Patent No.: US PP24,294 P3
(45) Date of Patent: Mar. 4, 2014

(54) ***PHYGELIUS* PLANT NAMED 'LEMON SPRITZER'**

(50) Latin Name: *Phygelius×rectus*
Varietal Denomination: Lemon Spritzer

(76) Inventor: Ann Elizabeth Detweiler, Albany, OR (US)

( * ) Notice: Subject to any disclaimer, the term of this patent is extended or adjusted under 35 U.S.C. 154(b) by 126 days.

(21) Appl. No.: 13/506,805

(22) Filed: May 16, 2012

(65) Prior Publication Data

US 2013/0312148 P1 Nov. 21, 2013

(51) Int. Cl.
*A01H 5/00* (2006.01)

(52) U.S. Cl.
USPC ..... Plt./468

(58) Field of Classification Search
USPC ..... Plt./468
See application file for complete search history.

*Primary Examiner* — Howard Locker
(74) *Attorney, Agent, or Firm* — Klarquist Sparkman, LLP

(57) ABSTRACT

A new and distinct cultivar of *Phygelius* plant characterized by its variegated yellow leaves that are speckled and blotched with lime and pine green.

2 Drawing Sheets

Botanical denomination: *Phygelius×rectus*.
Variety denomination:
'Lemon Spritzer'.

BACKGROUND OF THE INVENTION

The present invention relates to a new and distinct cultivar of *Phygelius*, given the name, 'Lemon Spritzer'. *Phygelius* is in the family Scrophulariaceae. This plant is a found whole plant mutation of *Phygelius×rectus* 'Sunshine', an unpatented plant. It was found at a nursery in Albany, Oreg. This cultivar was selected for its lovely variegation.

Compared to the parent plant, *Phygelius* 'Sunshine', the new cultivar has yellow leaves that are speckled and blotched with lime and pine green rather than just yellow.

*Phygelius* 'Lemon Spritzer' is uniquely distinguished by its variegated yellow leaves that are speckled and blotched with lime and pine green. It is the only variegated *Phygelius* on the market known to the inventor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
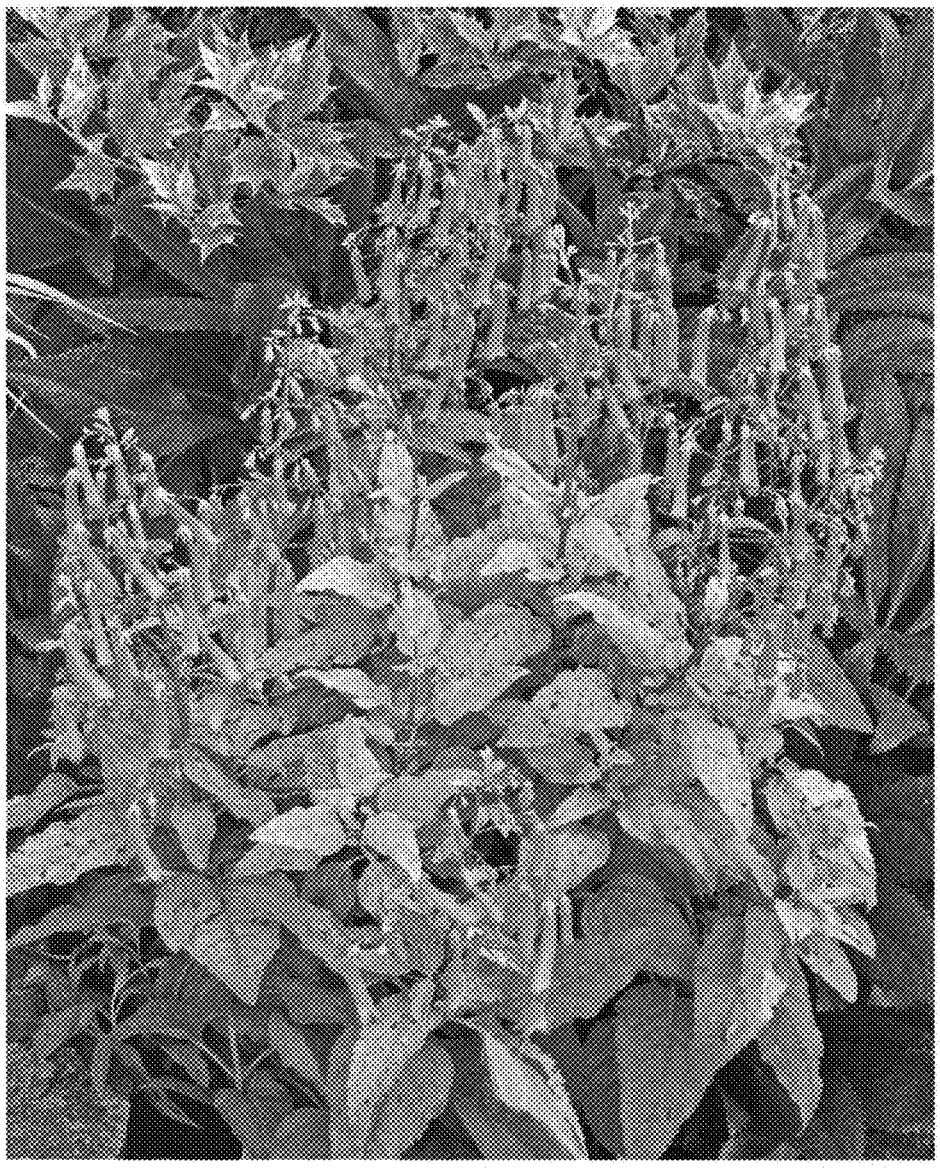
FIG. 1 shows a close up of a one-year-old *Phygelius* 'Lemon Spritzer in the summer in Canby, Oreg.
Figure 2:
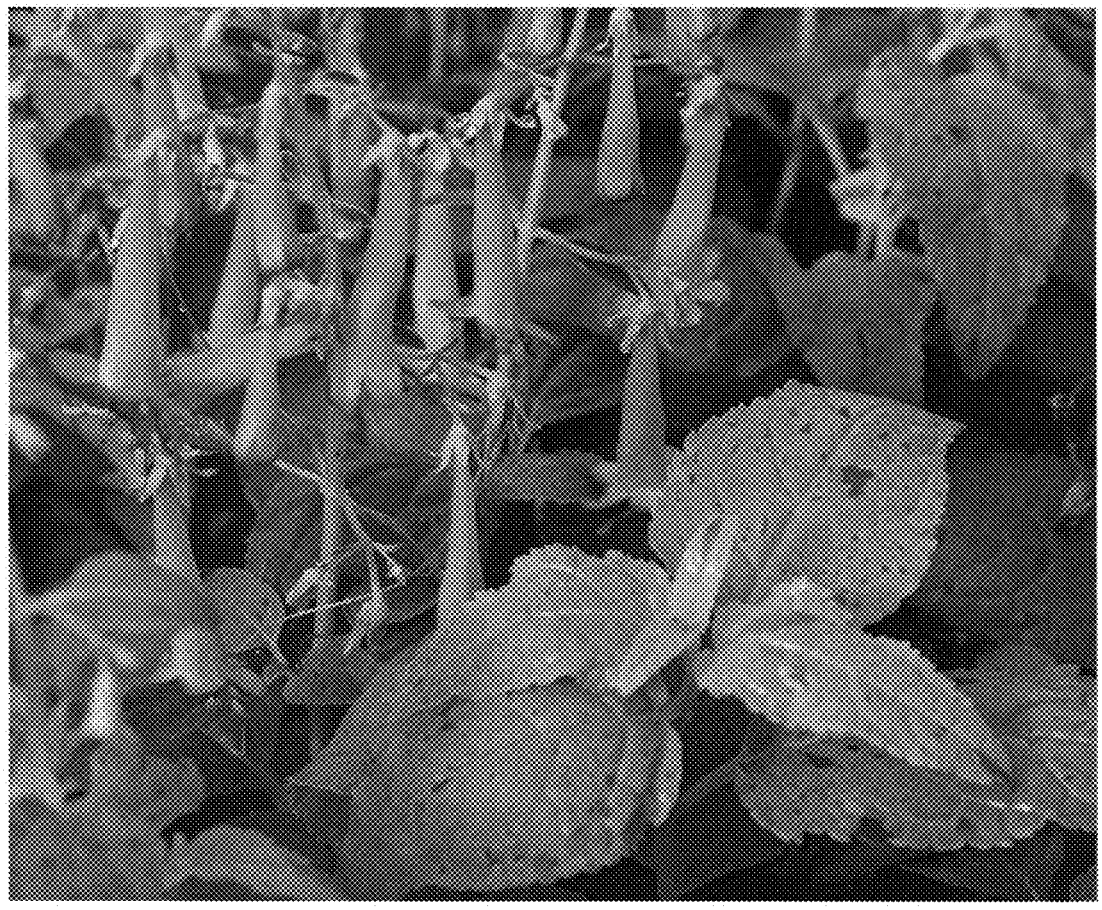
FIG. 2, foreground, shows a two-year-old *Phygelius* 'Lemon Spritzer' in bloom growing in full sun in the garden in late summer in Canby, Oreg.

The following is a detailed description of the new *Phygelius* cultivar based on observations of one-year-old specimens grown outside in one gallon pots in Canby, Oreg. in late September. The color descriptions are all based on The Royal Horticultural Society Colour Chart, 5$^{th}$ edition except where general color terms of ordinary dictionary significance are used.

Plant:
- *Type.*—Semi-evergreen subshrub.
- *Form.*—Upright, branching.
- *Cold hardiness.*—USDA Zone 7-10.
- *Size.*—Grows to 91 cm wide and 91 cm high.
- *Vigor.*—Excellent.
- *Stem number.*—3 main stems from the crown.
- *Stem.*—Upright, grows to 45 cm long and 18 mm wide (at the base), glabrous, internodes grow to 4 cm long, Greyed Purple 187A on older stems, younger stems Greyed Purple 184B.
- *Rooting.*—Plants root easily from stem cuttings.

Leaf:
- *Type.*—Simple.
- *Arrangement.*—Opposite.
- *Shape.*—Ovate to ovate lanceolate.
- *Venation.*—Pinnate.
- *Margins.*—Serrate.
- *Apex.*—Acute.
- *Base.*—Cuneate.
- *Blade size.*—Grows to 7.5 cm long and 4 cm wide.
- *Petiole.*—Grows to 18 mm long and 2 mm wide, Greyed Orange 177A.
- *Surface texture.*—Glabrous on both sides.
- *Leaf color.*—Topside closest to Yellow Green N144A speckled and blotched with Green 137D and Yellow Green 146B with main vein at base Greyed Orange 177A, bottom side Yellow Green 146D with darker spots of Yellow Green 147C.

Inflorescence:
- *Type.*—One-sided, pyramidal panicle with pendulous flowers.
- *Number of flowers per inflorescence.*—About 60.
- *Size of inflorescence.*—Grows to 19 cm long and 8 cm wide.
- *Peduncle.*—Grows to 4.5 cm long and 3 mm wide, glabrous, Greyed Orange 177A.

*Pedicel.*—Grows to 1 cm long and 1 mm wide, glabrous, Red 46A.

*Bloom period.*—June to November in Canby, Oreg.

Flower bud:

*Size.*—3.5 cm long and 7 mm wide at the widest area.

*Description.*—Tubular, pendulous.

*Color.*—Red 47B on bottom ⅔ and Greyed Red 181C on top ⅓.

Flower:

*Type.*—Zygomorphic, perfect.

*Shape.*—Tubular.

*Size.*—Grows to 4 cm long and 4.5 cm wide.

*Corolla description.*—Grows to 4 cm long and 2 cm wide; glabrous inside and out; tube 3.2 mm long, swollen to 6.5 wide on bottom side for 5 mm under the calyx then narrows to 5 mm wide and expanding to 9 mm wide below the lobes; lobes reflexed, oblong, tips obtuse, margins entire, top two lobes 7 mm long and 6 mm wide, bottom three lobes 7 mm long and 5 mm wide; outside color between Greyed Red 181 C and Red 47B, inside color Red 53B on the first 5 mm of the lobes then Yellow 12A for 9 mm then Yellow 12D.

*Calyx description.*—5 mm deep and 12 mm wide, 5 spreading, recurved lobes cut almost to the base, glabrous inside and out, each lobe lanceolate in shape, 7 mm long and to 2 mm wide, margins entire, tip acute, Yellow Green 144B tinted Greyed Orange 176A.

*Pistil description.*—1, 54 mm long, ovary 6 mm long and 3.5 mm wide, Yellow Green 144B tinted Greyed Purple 185A; style 49 mm long and less than 1 mm wide, Greyed Purple 185A; stigma Greyed Purple 187A.

*Stamen description.*—4, filaments: two short 2 cm long and two long 2.2 cm and 1 mm wide, Red Purple 60A, anthers 3 mm long and 2 mm wide, Greyed Green 195A, pollen Greyed Brown N199A.

*Fragrance.*—None.

*Lastingness.*—A flower lasts about a week on a plant.

Fruit:

*Type.*—Capsule, curved.

*Fertility.*—Poor.

*Size.*—1 cm deep and 5 mm wide.

*Color.*—Brown 200D.

Seed: None seen.

Pests and diseases: Plants of the new *Phygelius* have not been observed to be resistant to pathogens and pests common to *Phygelius*.

I claim:

1. A new and distinct cultivar of *Phygelius* substantially as shown and described.

* * * * *